United States Patent
Vanheule et al.

(10) Patent No.: US 11,497,556 B2
(45) Date of Patent: Nov. 15, 2022

(54) PRE-OPERATIVE DETERMINATION OF IMPLANT CONFIGURATION FOR SOFT-TISSUE BALANCING IN ORTHOPEDIC SURGERY

(71) Applicant: MATERIALISE N.V., Leuven (BE)

(72) Inventors: Valentine Vanheule, Leuven (BE); Roel Wirix-Speetjens, Leuven (BE); Hendrik Delport, Leuven (BE)

(73) Assignee: Materialise, NV, Leuven (BE)

( * ) Notice: Subject to any disclaimer, the term of this patent is extended or adjusted under 35 U.S.C. 154(b) by 760 days.

(21) Appl. No.: 16/060,219

(22) PCT Filed: Dec. 14, 2016

(86) PCT No.: PCT/US2016/066581
§ 371 (c)(1),
(2) Date: Jun. 7, 2018

(87) PCT Pub. No.: WO2017/106294
PCT Pub. Date: Jun. 22, 2017

(65) Prior Publication Data
US 2018/0360544 A1 Dec. 20, 2018

Related U.S. Application Data (60) Provisional application No. 62/268,872, filed on Dec. 17, 2015.

(51) Int. Cl.
*A61B 34/10* (2016.01)
*A61B 17/56* (2006.01)
(Continued)

(52) U.S. Cl.
CPC .............. *A61B 34/10* (2016.02); *A61B 17/56* (2013.01); *A61B 17/17* (2013.01);
(Continued)

(58) Field of Classification Search
CPC ... A61B 34/10; A61B 17/56; A61B 2034/102; A61B 2034/104; A61B 2034/107;
(Continued)

(56) References Cited

U.S. PATENT DOCUMENTS

2005/0119661 A1* 6/2005 Hodgson .............. A61B 17/155
606/90
2010/0076563 A1 3/2010 Otto et al.
(Continued)

OTHER PUBLICATIONS

Bloemker KH, Guess TM, Maletsky L, Dodd K. Computational knee ligament modeling using experimentally determined zero-load lengths. Open Biomed Eng J. 2012;6:33-41. doi: 10.2174/1874230001206010033. Epub Apr. 2, 2012. PMID: 22523522; PMCID: PMC3325586. (Year: 2012).*
(Continued)

*Primary Examiner* — Brian S Cook
(74) *Attorney, Agent, or Firm* — Dinsmore & Shohl LLP (57) ABSTRACT

Certain embodiments described herein relate to systems and methods for determining implant configuration or design of implants by taking into account soft tissues and utilizing patient-specific simulations of activities of daily living.

19 Claims, 6 Drawing Sheets

(51) Int. Cl.
    *A61B 17/17*     (2006.01)
    *A61F 2/38*     (2006.01)
    *A61F 2/46*     (2006.01)

(52) U.S. Cl.
    CPC ... *A61B 2017/568* (2013.01); *A61B 2034/102* (2016.02); *A61B 2034/104* (2016.02); *A61B 2034/107* (2016.02); *A61B 2034/108* (2016.02); *A61F 2/38* (2013.01); *A61F 2002/4633* (2013.01)

(58) Field of Classification Search
    CPC .............. A61B 2034/108; A61B 17/17; A61B 2017/568; A61F 2/38; A61F 2002/4633
    USPC ............................................................ 703/7
    See application file for complete search history.

(56) References Cited

U.S. PATENT DOCUMENTS

| | | | |
|---|---|---|---|
| 2012/0041446 A1 | 2/2012 | Wong et al. | |
| 2014/0222390 A1* | 8/2014 | Asseln | A61B 34/10 703/1 |
| 2014/0244220 A1 | 8/2014 | McKinnon et al. | |
| 2014/0324403 A1* | 10/2014 | Gotte | A61B 90/37 703/2 |
| 2015/0265363 A1 | 9/2015 | White et al. | |
| 2016/0045317 A1* | 2/2016 | Lang | G05B 19/4099 700/98 |
| 2017/0162078 A1* | 6/2017 | Imhauser | G09B 23/30 |

OTHER PUBLICATIONS

R. B. Martin et al., Skeletal Tissue Mechanics © Springer Science+Business Media New York 1998 (Year: 1998).*

International Search Report and Written Opinion dated Sep. 6, 2017, issued in PCT/US2016/066581.

Choi, Hon Fair et al., "A Collective Approach for Reconstructing 3D Fiber Arrangements in Virtual Musculoskeletal Soft Tissue Models." Computational Biomechanics for Medicine. 2015. pp. 117-128.

Geier, A. et al., "Simulation of varying femoral attachment sites of medial patellofemoral ligament using a musculoskeletal multi-body model." DEGRUYTER. Current Directions in Biomedical Engineering 2015. vol. 1. pp. 547-551.

Ishikawa, Yuki et al., "Effect of Mediolateral Knee Displacement on Ligaments and Muscles around Knee Joint: Quantitative Analysis with Three-Dimensional Musculoskeletal Ligament Knee Model." Intelligent Autonomous Systems 12. AISC 194. pp. 447-456.

Marra, Marco A. et al., "A Subject-Specific Musculoskeletal Modeling Framework to Predict In Vivo Mechanics of Total Knee Arthroplasy." Journal of Biomechanical Engineering. Feb. 2015. vol. 137. pp. 1-12.

Moissenet, Florent et al., "A 3D lower limb musculoskeletal model for simultaneous estimation of musculo-tendon, joint contact, ligament and bone forces during gait." Journal of Biomechanics. 2014. vol. 47. pp. 55-58.

OpenSim, "User's Guide." Release 2.4. Stanford University. Apr. 4, 2012.

* cited by examiner

PRE-OPERATIVE DETERMINATION OF IMPLANT CONFIGURATION FOR SOFT-TISSUE BALANCING IN ORTHOPEDIC SURGERY

CROSS-REFERENCE TO RELATED APPLICATIONS

This application claims the benefit of U.S. Provisional Patent No. 62/268,872, filed Dec. 17, 2015. The content of the provisional application is hereby incorporated by reference in its entirety.

BACKGROUND

Field of the Invention

This application relates to positioning and design of implants in orthopedic surgery. More particularly, this application relates to systems and methods for determining implant configuration or design of implants by taking into account soft tissues and utilizing patient-specific simulations of activities of daily living.

Description of the Related Technology

In joint replacement surgery, the goal is generally to have the replacement joint function and feel as much like the healthy native joint as possible. For example, in knee replacement surgery (also referred to as total knee arthroplasty or TKA), the surgical goal is to create a symmetrically balanced flexion and extension gap. That is, the gap between the resected bones on each side of the joint should be the same both when the leg is straight and when the knee is bent. The extension gap is formed by the gap between the distal femoral resection and the tibial resection. The flexion gap is formed by the gap between the posterior femoral resection and the tibial resection. A combination of accurate bone resections and appropriate soft-tissue balancing determines the implant alignment, notably femoral component rotation. Improper implant positioning results in complications such as instability, anterior knee pain and poor patellar tracking.

Traditionally, two techniques are used to perform TKA: measured resection and gap balancing. Employing these different methods can often result in differences in femoral component rotation. Controversy exists, as some surgeons prefer the measured-resection method, while others think that gap balancing gives the best outcome.

Measured resection uses bony landmarks that are visible on medical images such as CT scans to determine the locations and angles of bone resection. The surgeon performs these bone resections at fixed, or 'measured', angles with respect to those anatomical landmarks of the femur and tibia. The goal of measured-resection techniques is to restore the alignment of the mechanical axis of the leg. Because bony landmarks are visible on medical images, pre-operative planning is available for this approach. In particular, medical images may be used to create three-dimensional models of the knee anatomy. Those models may be used to create patient-specific surgical guides which can be used to precisely locate both the bone resection and the implant locations. Nevertheless, some in the orthopedic surgical community contend that measured resection leads to substantial variation in the rotation and the sizing of the femoral component. Furthermore, basing implant position fully on the shape of the bony anatomy may lead to excessive ligament strains, leading to ligament releases in which parts of the ligament are cut in order to relieve tension. Because ligaments are critical to the stability of knees, it would be advantageous to leave the ligaments intact as much as possible during the procedure.

Gap-balancing techniques (also referred to as soft-tissue balancing), do not substantially rely on bony landmarks. Rather, the core of the soft-tissue balancing technique is that balanced tension in the collateral ligaments dictates the femoral bone resections. First, the proximal tibial bone cut is made—usually perpendicular to its mechanical axis. Subsequently, symmetrical tension is applied to the joint line in extension using a ligament tensor, spacer block or laminar spreader, or simply by holding the patient's leg by the calf and the ankle, and the distal femoral bone cut is made parallel to the tibial cut, based on the ligament tension. At this moment, intraoperative gap balancing is somewhat subjective and highly dependent on the surgeon's expertise. Moreover, all of the gap balancing is performed during the procedure, and it is not planned ahead of time. As a result, gap balancing solutions must be used intra-operatively, leading to prolonged operating times. Although some new technologies provide intraoperative assistance to surgeons in measuring forces and strains in the knees, they all tend to lead to prolonged operating times. Accordingly, improved techniques for determining optimal implant configurations are needed.

DETAILED DESCRIPTION OF CERTAIN INVENTIVE EMBODIMENTS

Embodiments disclosed herein relate to systems and methods for determining an implant configuration in a joint replacement procedure. The inventors have discovered that the use of patient-specific musculoskeletal models is an effective predictive tool in clinical practice. In particular, the inventors have discovered that running simulations which apply appropriately designed computer models enable surgeons to predict the functional outcomes of different surgical approaches. The functional outcomes can be compared to determine the best surgical approach in a particular case.

In some embodiments, gap-balancing knee-replacement surgery may be pre-operatively planned using inventive techniques disclosed herein. In these embodiments, a pre-operative scan of the patient's knee anatomy may be taken. Pre-operative scans of the patient's hip and ankle anatomy may also be taken. The scan data may be converted into a 3D model of the knee. Simulations of the kinematic behavior of the knee during certain activities, such as activities of daily living, with various different implant configurations may then be performed. These activities may include squatting, gait, chair rise, or other common movements of the knee. The simulations also generate information about the predicted kinematics and ligament strains of the knee with each potential implant configuration. In some embodiments, if one or more of the predicted ligament strains exceeds an upper threshold (such as 5-10% for example), the implant configuration may be rejected. One or more objective functions or criteria may provide an optimization goal for the simulation output to determine the optimal configuration for the knee implant. In some embodiments, the objective functions may be defined such that the optimal implant configuration is the one in which the predicted ratio of strain in collateral ligaments is as close to a predetermined value, such as 1, as possible during the entire range of motion. Other objective functions may not require simulation, and may instead relate to implant configurations determined to be the best fit by a measured-resection analysis. Many other objective functions may be used, individually, or as part of a weighted determination which uses several different objective functions and assigns them each a specific weight value in the overall optimization determination.

In some embodiments, using the 3D model of the knee, the kinematics of the native (untreated) knee may be approximated using a patient-specific native knee model. This patient-specific native knee model may provide reference values for the amount of ligament strain in knee ligaments as activities of daily living are simulated. Objective functions may be then defined in terms of the relative similarity of the implant configuration to the native knee kinematics and ligament strain. In addition, using the bony landmark information from the initial scan of the anatomy, an additional objective function may be defined in terms of the mechanical alignment of the axis of the knee with each implant configuration considered for simulation. In these embodiments, advantages associated with the measured-resection approach may be combined with the advantages realized from gap-balancing approaches.

By providing quantitative information pre-operatively and determining the optimal implant configuration prior to the procedure, time-consuming intra-operative ligament balancing can be reduced or even avoided entirely. Potentially damaging ligament releases can also be avoided. In addition, using the inventive techniques disclosed herein, knee stability can be investigated for the full range of the knee's motion, and not merely in two positions (flexion and extension) as is the case with conventional approaches. By investigating stability throughout the entire range of motion, instability at mid-flexion can be identified and addressed. Finally, by obtaining a pre-operative determination of implant configuration, no navigation system is needed during the procedure to assess stability in the joint.

Figure 1:
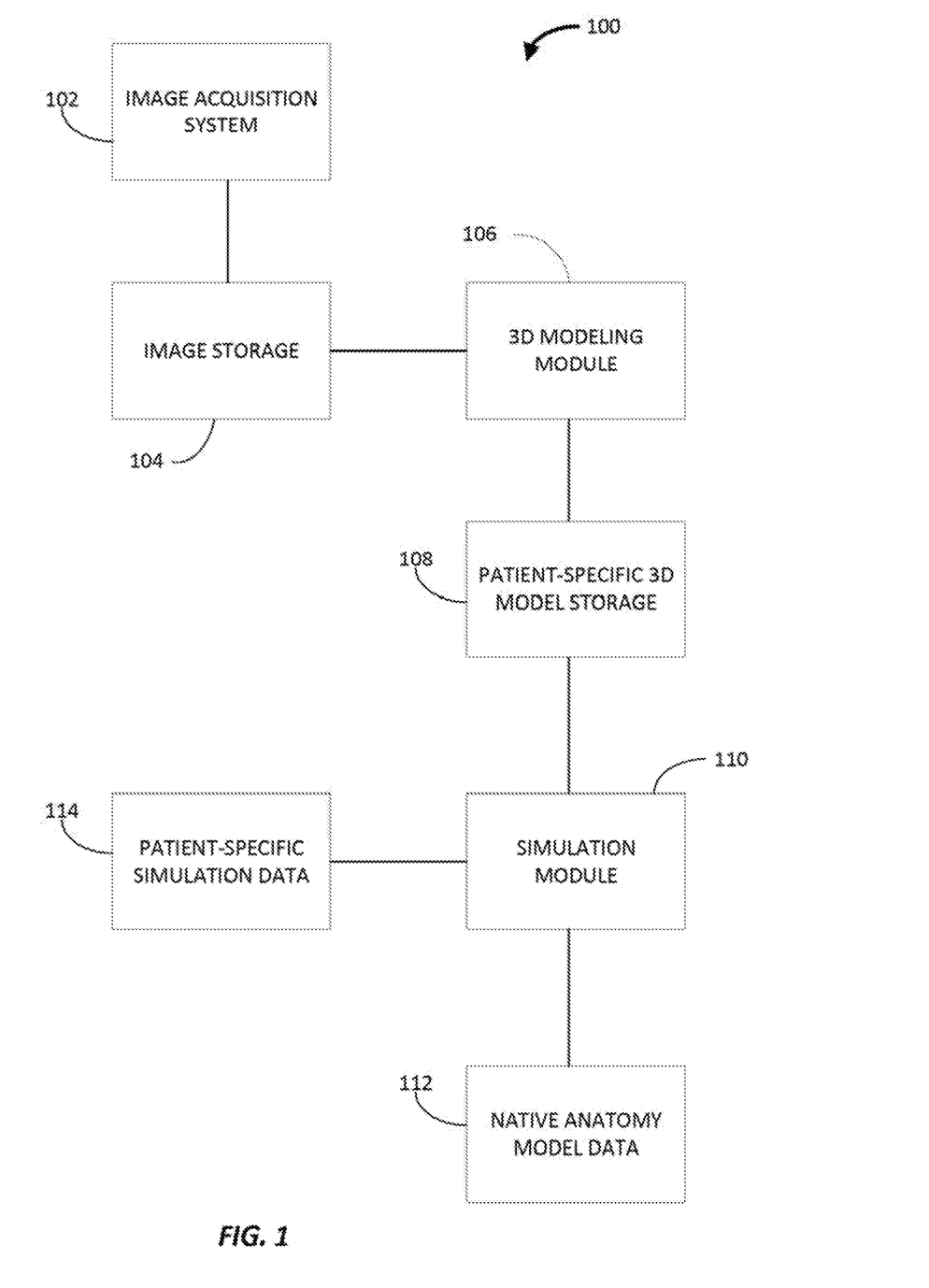
FIG. 1 is a block diagram providing high-level view of a computerized system environment 100 which may be used to practice various embodiments described herein.

FIG. 1 is a block diagram providing high-level view of a computerized system environment 100 which may be used to practice various embodiments of the invention. As noted above, in accordance with various embodiments, medical images may be obtained from a patient in order to model and simulate motion and forces within the relevant joint of the patient. As such, the system environment may include an image-acquisition system 102. The image-acquisition system 102 is generally configured to scan the joint anatomy and surrounding areas of the patient and to record the image data generated during those scans. The image-acquisition system 102 may take various forms. In some embodiments, the image-acquisition system 102 may be an x-ray machine that records images of the patient's bone structure. In some embodiments, it may be a computer tomography ("CT") scanner which may build images by combining a series of x-ray images taken from different angles to produce slices of specific areas of a scanned object. In still other embodiments magnetic resonance imaging ("MRI") may be used. Other scanning technologies are also suitable.

Irrespective of the particular image-acquisition system 102 used, the images obtained using the image-acquisition system 102 may be stored in image storage 104. Image storage 104 may be a computer system that is designed particularly to store medical image data. The image storage 104 may be a PACS system, for example. Alternatively, the image storage 104 may be a more general-purpose computer system having sufficient storage capacity to store medical images obtained from patients. The image storage 104 may be electronically connected to the image-acquisition system 102. The connection may be a computer network connection which is configured to route the image data over the network from the image-acquisition system 102 to the image storage 104. The connection may be a more direct connection such as a physical serial connection. The image storage 104 may be configured to allow access to the image data by a 3-D modeling module 106. The 3-D modeling module 106 is a computerized software and/or hardware module which is capable of converting the image data stored in image storage 104 into a 3-D model of the patient anatomy. In some embodiments, the 3-D modeling module 106 may be configured to extract patient-specific bone geometry from the medical image data received from image storage 104 using imaging techniques. In some embodiments, the 3-D modeling module 106 may also be configured to extract patient-specific cartilage geometry from the medical image data received from image storage 104 using imaging techniques. The 3-D modeling module 106 may further determine one or more bony landmarks which are used to define reference systems and soft tissue attachments within and around the joint. The 3-D modeling module 106 may be connected to the image storage 104 via a network connection. Alternatively, the 3-D modeling module 106 may reside on a standalone computer which receives image data extracted from image storage 104 via removable storage media such as a portable hard drive, a USB storage device, or some other type of removable storage. In some embodiments, the 3-D modeling module 106 may take the form of 3-D modeling software such as the Mimics Innovation Suite from Materialise NV of Leuven, Belgium.

Using the 3-D modeling module 106, a 3-D model of the relevant anatomy may be created. The 3-D model may be in the form of a CAD file, an STL file, or some other three-dimensional file format. Once the 3-D model has been created, it may be stored in patient-specific 3-D model storage 108. The patient-specific 3-D model storage 108 may be data storage located on the same computing device as the 3-D modeling module 106, or it may be separate dedicated storage which is configured to receive and store 3-D models of patient anatomy.

The patient-specific 3-D model storage 108 may be in data communication with a simulation module 110. The simulation module 110 may take the form of computer hardware and/or software that is designed to simulate the mechanics of the relevant patient anatomy working in concert with its environment. The simulation module 110 may be loaded on a special-purpose computer which is designed to perform simulations. Alternatively, the simulation module may take the form of a software application that is stored and executed on a general-purpose computer. In some embodiments, the simulation module 110 may be on the same computing device as the 3-D modeling module 106 and the patient-specific 3-D model storage 108. The simulation module 110 may, in some embodiments, be a commercial off-the-shelf simulation software system such as the Any-Body Modeling System™ provided by AnyBody Technology A/S of Aalborg, Denmark. The simulation module 110 may also be an open-source project such as the OpenSim software platform which performs simulation of human activity and movement. In other embodiments, the simulation module 110 may be a fully customized simulation software solution developed specifically to measure and predict kinematics of native and treated patient anatomy.

The simulation module 110 may be configured to receive patient-specific 3-D models, and perform simulations to produce patient-specific simulation data 114. As will be discussed in more detail below, the patient-specific simulation data 114 generally provide detailed information about movement and forces acting within the joint during activities typically performed by the joint during daily living. These activities are commonly referred to as activities of daily living ("ADL"). In some embodiments simulation module 110 may be configured to perform simulations of various different arthroplasty implant configurations in order to determine the optimal location for placement of the implants. The patient-specific simulation data 114 may be stored within the simulation module 110. Alternatively, the patient-specific simulation data 114 may be stored separately in a dedicated simulation storage memory.

The system environment 100 may also include native anatomy models 112. As will be discussed in detail below, the native anatomy models 112 may be used as reference values for determining whether and how a simulated implant configuration meets a predefined objective. Additional details about the native anatomy models will be discussed below in connection with FIG. 2.

Figure 2:
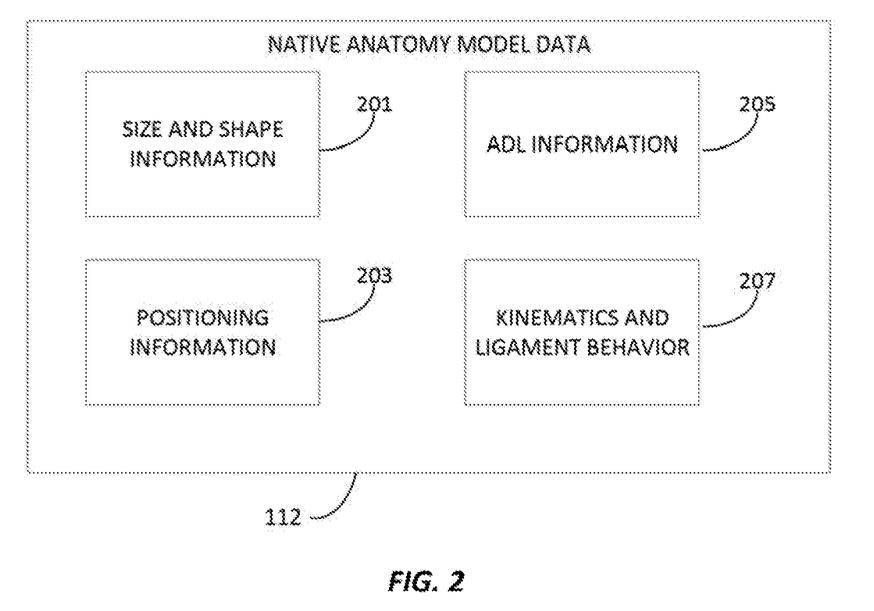
FIG. 2 is a block diagram providing a more detailed view of the native anatomy model data shown in FIG. 1.

FIG. 2 is a block diagram providing a more detailed view of the native anatomy model data 112 described in FIG. 1. The native anatomy model data 112 may include data obtained from kinematic testing of the native joint, i.e. the pre-operative joint. In some embodiments, the native anatomy model data 112 may include data obtained by simulating the native joint during activities of daily living.

As shown, the native anatomy model data 112 may include size and shape information 201. The size and shape information 201 may include information about the sizes and shapes of the anatomical features relevant to the joint of the patient. For example, in the context of the knee joint, the size and shape information 201 may include the length of the femur, the size (e.g., diameter) of the femoral head, the length of the tibia, the size of the tibial plateau, and other size information. The size and shape information 201 may also include shape information about the femoral condyles, the tibial plateaus, the trochlear groove, and other shape information.

The native anatomy models 112 also may include positioning information 203. Positioning information 203 may include information that pertains to the relative positions of the various anatomical features within the joint of the patient. For example, in the context of the knee, positioning information may relate to the angle of the mechanical axis of the knee, soft-tissue attachment locations, ligament positioning, and the like. The native anatomy models 112 may also include information related to activities of daily living 205 ("ADL information"). The ADL information 205 may include data related to routine movements, motions, and activities which relate to the joint.

The native anatomy models 112 also may include kinematic and ligament behavior information 207. The kinematic and ligament behavior information 207 generally provides information relating to motion of the joint of the patient, and forces and stresses placed on different areas in or around the joint during activities of daily living. The kinematic and ligament behavior information 207 may include information which results from a kinematic simulation of the native joint of the patient. Thus, the native anatomy model 112 may provide information which indicates that the native knee, having a specific physical profile (e.g., a particular size, soft-tissue attachments, and mechanical axis angle), has a particular kinematic profile that is associated with one or more ADLs. Thus, the native anatomy models 112 may be used to determine the behavior of the native knee of the patient.

In some embodiments the size and shape information 201 may be corrected from a diseased condition to an intact/healthy condition by using statistical shape models which are used to predict the intact/healthy geometry of a patient anatomy based on the structural aspects of the native anatomy.

Figure 3:
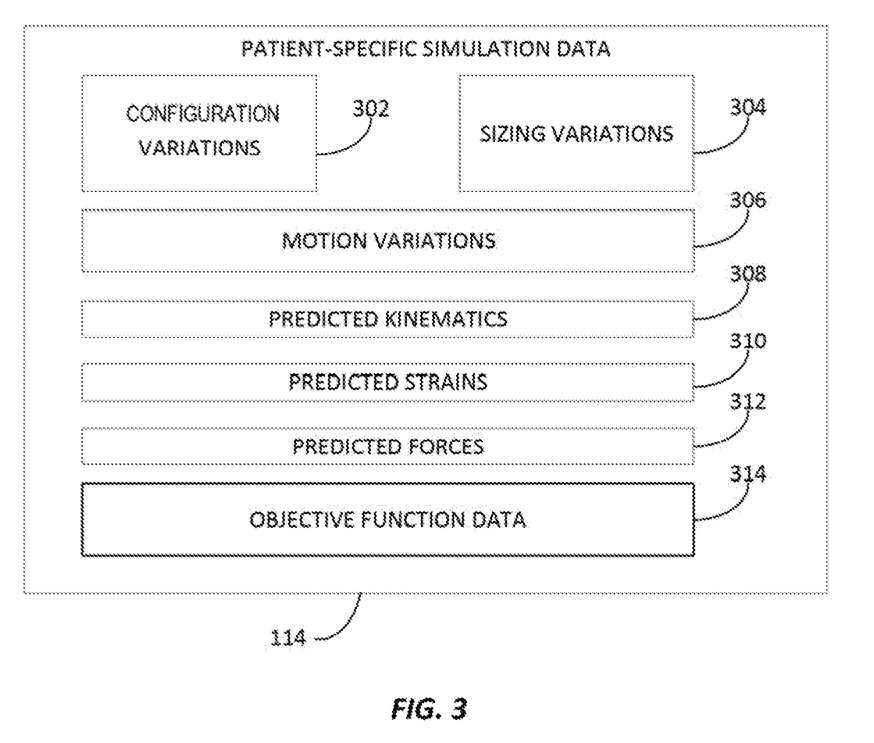
FIG. 3 is a block diagram providing a more detailed view of the patient-specific simulated simulation data shown in FIG. 1.

FIG. 3 is a block diagram providing a more detailed view of the patient-specific simulation data 114 shown in FIG. 1. As discussed above, the patient-specific simulation data 114 are generated by the simulation module 110 based on medical image information about the patient anatomy that is input to the simulation module. In particular, the simulation module 110 may be configured to receive patient-specific 3-D models, and perform simulations to produce patient-specific simulation data 114. In some embodiments, simulation module 110 may be configured to perform simulations of various different implant configurations that may be placed within the joint as part of an arthroplasty procedure. The simulations may simulate various different variables which can impact the surgical outcome and patient satisfaction with the procedure. In some embodiments simulation module 110 may be configured to perform simulations of various different arthroplasty implant configurations in order to determine the optimal location for placement of the implants. The simulation module 110 may model scenarios having different data variables in producing the patient-specific simulation information 114. The different data variables used in connection with any simulation may be stored within the patient-specific simulation information 114 in order to demonstrate how different surgical approaches and implant configurations impact the kinematic profile or ligament behavior of a surgically repaired joint.

For example, the simulation module 110 may conduct a series of simulations that consider configuration variations 302 in the placement or the shape of the implant. In some embodiments, these various placement locations may be associated with the location, angle, and/or orientation of the bone resections that may be needed in order to complete the arthroplasty procedure. In some embodiments, these configuration variations 302 may be associated with different designs for the articulating surfaces of the implant. For example, in the case of a knee arthroplasty, various different placement locations for both the femoral component and the tibial component may be simulated. These various placement locations may be identified based on the different angles and locations of the bone cuts that are available to the surgeon in carrying out the procedure. The simulation module 110 may also create patient-specific simulation data which simulates sizing variations 304. Sizing variations 304 may include variations in the size of one or more of the devices to be implanted in the patient, or in the size of surgical tools that may be used in the procedure, such as surgical guides or other instrumentation. Sizing variations 304 may also relate to the size or degree of ligament release contemplated by a particular surgical approach or configuration.

Patient-specific simulation data 114 generated by the simulation module 110 also may model specific positions and sizes in the context of certain movements of the joint. In some embodiments, these movements may be activities of daily living. Accordingly, the patient-specific simulation data 114 may include motion variation data 306. In some embodiments, a patient-specific simulation may be constructed to simulate a specific type of movement (such as an ADL) for one or more configuration variations 302 and sizing variations 304. The patient-specific simulation data 114 may include predicted kinematics 308 which represent the predicted movements within the joint for a particular simulation scenario. The patient-specific simulation data 114 may also include predicted strains 310. The predicted strains 310 may be strains associated with ligaments which are impacted by movement within the joint. For example, in the context of the knee joint, predicted strains may involve the amount of strain on the collateral ligaments (LCL and MCL) and may include the cruciate ligaments (ACL and PCL) across the range of motion of a particular ADL such as, for example, squatting. The patient-specific simulation data 114 may also include predicted forces 312. Predicted forces 312 may relate to compressive forces acting on specific areas within or around the joint. For example, in the context of the knee joint, predicted forces 312 may include contact forces in the medial and lateral compartments of the implant across a range of motion being simulated by the simulation module 110. Predicted forces 312 may also include compressive forces against or stresses within a bone across the simulated range of motion.

Patient-specific simulation data 114 may also include objective function data 314. The objective function data 314 generally includes information which is used to evaluate the simulation results. More particularly, the objective function data 314 may provide a basis for comparing different surgical approaches and implant configurations to determine which of those approaches and/or implant configurations are likely to provide the best surgical outcome. As will be discussed in additional detail below, objective functions may take various forms. In some embodiments, the objective function data 314 may define functions in terms of the ratio of strain in ligaments within the joint during a simulated range of motion. Other objective functions may relate to the kinematics of the joint.

Still other objective functions may relate to comparisons of kinematics or ligament behavior in the simulated joint with those of the native joint. The information regarding the native knee may be provided by the native anatomy model data 112. The information may be provided by simulating movement in the pre-operative joint based on the imaging data obtained for the diseased joint. Alternatively, the intact/healthy joint can be modelled by using statistical shape models to correct the geometry obtained from the 3-D image of the diseased knee obtained via a medical image scan. In these implementations, the kinematics and ligament behavior of the native knee can be determined without requiring gait analysis of the patient. In one particular example, the native ligament strain in a knee may be determined by applying an equation $\varepsilon=(L-L_r)/L_r$, wherein $\varepsilon$ is the ligament strain, and wherein L is ligament length, and wherein $L_r$ is ligament reference length. Other equations may also be applied. For example, the equation $\varepsilon=(L-L_0)/L_0$, may also be applied, wherein $\varepsilon$ is the ligament strain, and wherein L is ligament length, and wherein $L_0$ is ligament slack length. The ligament slack length $L_0$ may be computed using the equation $L_0=L_r/(\varepsilon_r+1)$, where $L_r$ is the ligament reference length and $\varepsilon_r$ the reference strain. In general, any number of objective functions may be defined for a particular set of patient-specific simulation data 114. Moreover, a combination of objective functions may be defined which are used to evaluate a specific implant configuration. Though not requiring gait analysis, in some embodiments the simulations in these implementations may still require establishing patient-specific ligament parameters. This can, for instance, be achieved by means of joint laxity measurements. In other embodiments, a probabilistic approach can be followed, using statistical values for ligament parameters. In such implementations, the kinematics and ligament behavior of the native knee can be determined without requiring any physical activity on the part of the patient.

Figure 4:
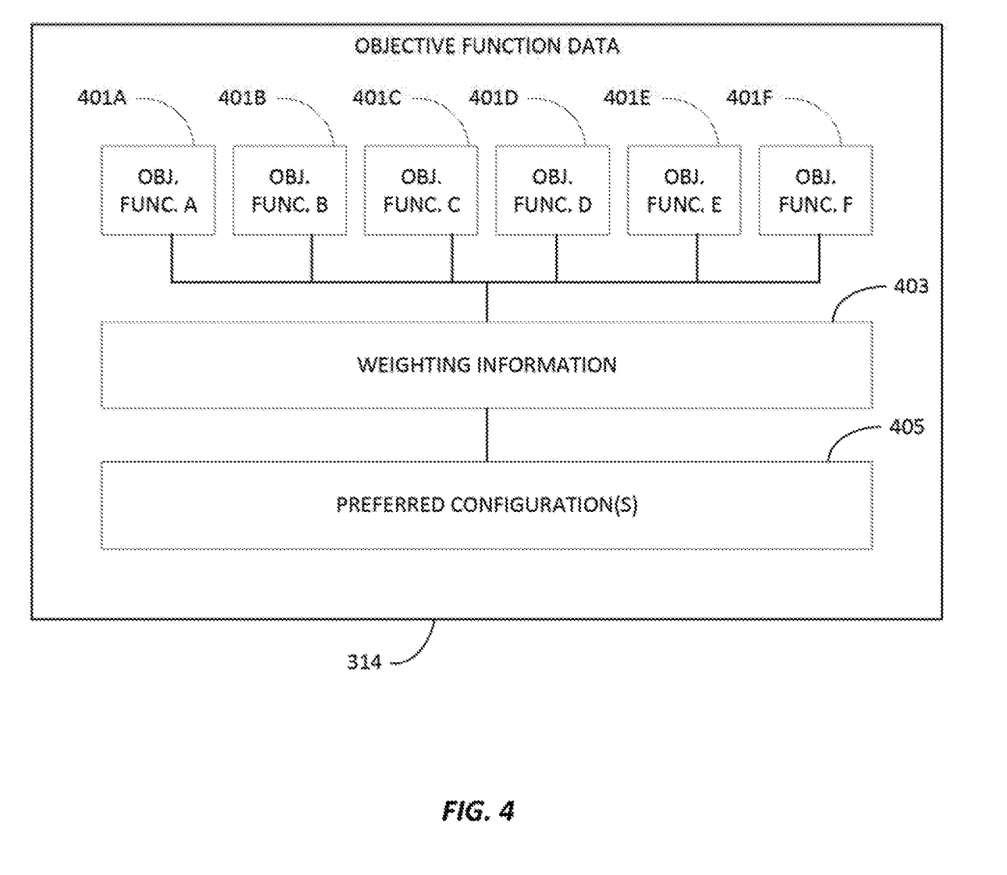
FIG. 4 is a block diagram providing a more detailed view of objective function data shown in FIG. 3.

Turning now to FIG. 4, a more detailed view of the objective function data 314 is provided. As discussed above, patient-specific simulations may utilize a plurality of objective functions to evaluate the simulated movements and determine a best surgical approach. As shown in FIG. 4, the objective function data 314 may include several objective functions 401A-401F. Each of these objective functions may be predefined and stored in a function library made available to the user performing the simulation using simulation module 110. The objective functions 401A-401F may also be user-defined at the time simulations are performed.

In the context of the knee joint, the inventors have discovered that certain objective functions are useful to determine the best surgical implant location for a joint arthroplasty procedure. In one particular embodiment, the procedure is a TKA procedure performed on the knee joint. However, the knee procedure could also be a partial knee arthroplasty, a unicondylar knee arthroplasty, or a patella-femoral-joint arthroplasty. One objective function holds that the ratio of strain in collateral ligaments (MCL and LCL) of the knee should be as close to a predetermined value, such as 1, as possible during whole range of motion. Thus, if a simulation of an ADL (or some other movement) is performed using many different possible implant configurations, the configuration having the ratio of strain closest to the predetermined value (between the MCL and LCL) throughout the range of motion will be considered the best configuration in the context of this objective function. Objective functions may also be defined based on a linear combination of the predicted ligament strains. One such objective function holds that the implant configuration having the lowest total ligament strain throughout the range of movement would be an optimal configuration.

Another objective function that may be used relates to the ratio of contact forces in the medial and lateral compartments of the implant. The objective function may be defined such that an optimal configuration maintains a ratio between the contact forces in the medial and lateral compartments of the implant as close to a predetermined value, such as 1, as possible throughout the range of motion (or ranges of motions) being simulated.

In some embodiments, the native or untreated knee may be used to form an objective function for evaluation. For example, an objective function may be applied in which the ligament strains of the repaired knee should approximate strains of the native knee as closely as possible throughout the entire range of motion being simulated. As noted above, in these implementations, the native anatomy model data 112 may be used to determine what the native strains are in the pre-surgical knee of the patient.

In addition to ligament behavior, kinematics of the knee may be used in connection with an objective function. For example, an objective function may be defined in which the kinematics of the treated knee should approximate the kinematics of the native knee throughout the range of motion of certain ADLs. Again, the native anatomy model data 112 may be used as a basis for comparison. Although specific objective functions have been described herein, it is to be appreciated that any type of objective function may be defined and utilized in accordance with embodiments of the inventions disclosed herein.

Turning back to FIG. 4, the objective function data 318 may also include weighting information 403. The weighting information 403 is typically used in a scenario where multiple objective functions have been defined for use in the context of a patient-specific treatment scenario. The weighting information 403 may be used to determine how much weight to allocate to each of the objective functions under consideration. For example, as shown in FIG. 4, several different objective functions such as objective functions 401A-401F may be used to determine the optimal implant configuration for a patient. The professional conducting the surgical planning (such as the surgeon), for example, may decide that certain objective functions should carry more weight in the determination than others.

For example, the surgeon may decide that the important objective function is the ratio of strain in the collateral ligaments, while the kinematics of the treated knee are not considered as decisive. The weighting information 403 may assign weighting values to each of the objective functions. Accordingly, when the results of each of the objective functions have been determined, they may be combined using the weighting information to result in an overall scoring of each simulated implant configuration. The configurations with the overall scores which are the highest after applying the weighting formation 403 may be considered the preferred configurations 405 as shown in FIG. 4. In some embodiments, a single preferred configuration 405 may be defined based on a simulation for a patient. Alternatively, a plurality of different preferred configurations 405 may be provided from which a surgeon may exercise his or her professional judgment in selecting among them based on factors ancillary to the simulation output.

Figure 5:
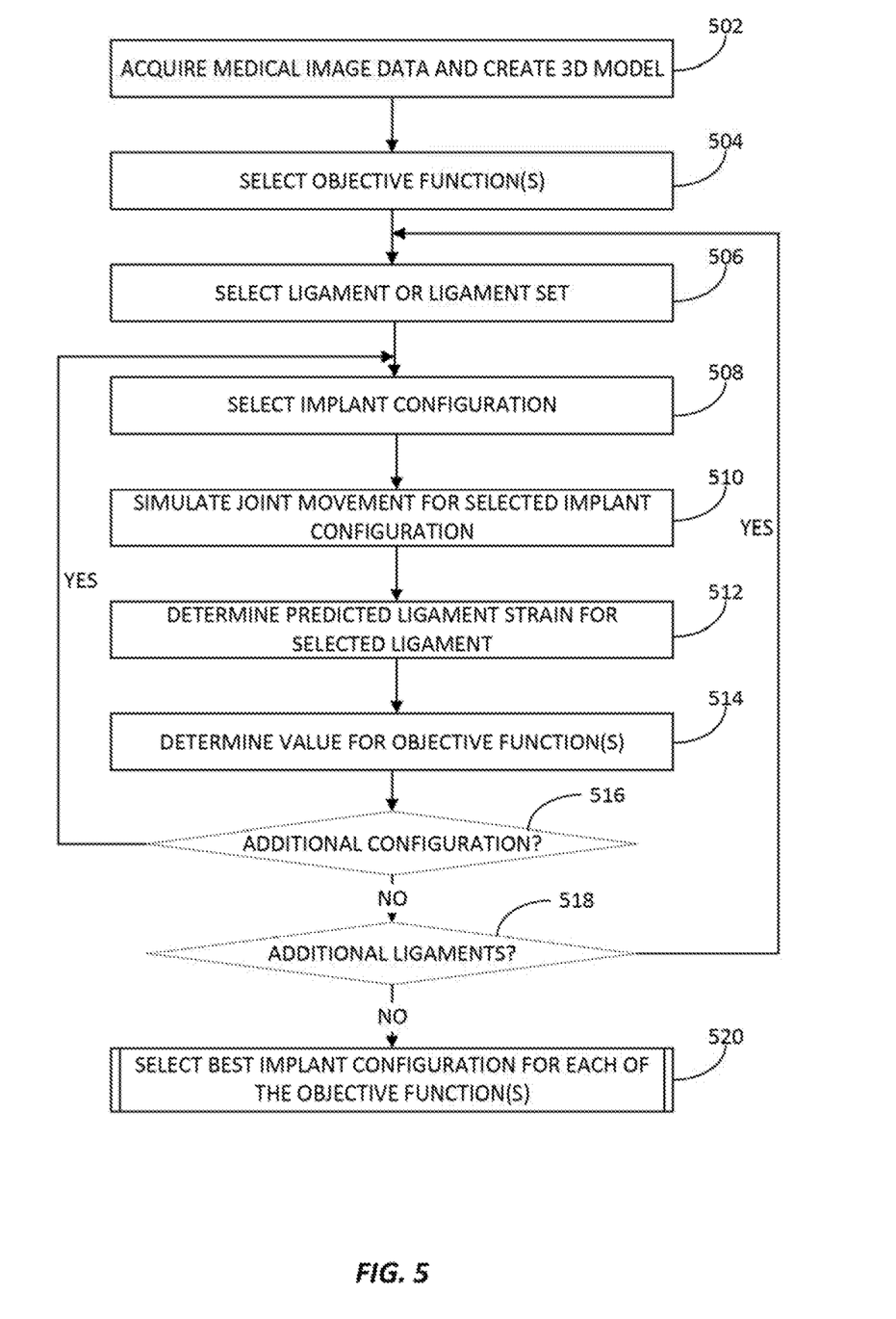
FIG. 5 is a flow chart providing one example of a process by which an optimal implant configuration for an orthopedic implant can be determined.

Utilizing systems such as, for example, the system environment 100 described in FIG. 1 above, the method of determining an optimal configuration for an orthopedic implant can be determined. FIG. 5 is a flow chart providing one example of a process by which an optimal configuration for an orthopedic implant can be determined. The process begins at block 502, where medical image data for the relevant anatomy may be acquired and a 3-D model may be created from the medical image data. As noted above, medical image data may include MRI data, X-ray data, CT data, ultrasound data, or some other type of scan of the patient joint anatomy. A 3-D representation of the scanned anatomy may be derived from the medical image information. The 3-D model, as noted above, may be created using CAD software or some other 3-D modeling software. In creating the 3-D representation/model of the patient's anatomy, one or more statistical shape models may be used to correct the raw 3-D model from a diseased condition to a healthy condition. The corrected model may be used to determine the behavior and structure of the native joint. Generating the 3-D model may also entail an identification of bony landmarks (in some cases using statistical shape models) which may be used to define reference systems and soft tissue attachments within the joint.

Next, the process moves to block 504 where one or more objective functions may be selected for use in determining the optimal implant configuration or optimal group of implant configurations. As noted above, the objective functions may be predefined and stored in some sort of function library. Alternatively, the objective functions may be user-defined either before or as part of the configuration determination process. The process next moves to block 506. There, one or more ligament(s) may be selected for analysis. For example, the user may determine that analysis of strain in a particular ligament should be determined so that the behavior of that ligament may be used in connection with one of the selected objective functions. In some implementations, upper thresholds for predicted ligament strain may be set for the selected ligament, so as to avoid damage to the ligament and the need for ligament release. In some implementations, lower thresholds for predicted ligament strain may be set for the selected ligament, so as to avoid instability of the joint. Next, the process moves to block 508 where a provisional implant configuration is selected for testing. Based on the 3-D model generated at block 502, an initial provisional implant configuration may be selected. In the context of the knee, the initial implant configuration may be selected based, for example, on the implant configuration suggested by a measured-resection analysis. In other words, the initial provisional implant configuration may be selected based on a measured-resection analysis that suggests a particular location for one or more of the orthopedic implants used in the procedure.

As noted above, typically, the implant will be a joint prosthesis that is used in connection with an arthroplasty procedure. In these cases, the implant may take the form of a joint prosthesis that has a plurality of mutually detached or detachable components. For example, the plurality of mutually detached or detachable components may be at least one of a femoral implant, a partial femoral implant and a unicondylar femoral implant; and at least one of a tibial implant, a partial tibial implant and a unicompartmental tibial implant. The plurality of mutually detached or detachable components may also include a spacer or a liner. In selecting a provisional implant configuration, it is to be understood that the implant configuration may be selected for each of the components. It is also to be understood that this step may comprise the selection of any of the components from a library of components of different shapes or sizes, or the design of patient-specific instances of any of the components or any part of the components. For example, the provisional, optimal or preferred implant configurations may refer to varying designs for the shape of the articulating surfaces of patient-specific implants in their spatial relationship to the patient's anatomy.

Once the provisional implant configuration has been selected, the process moves to block 510 where joint movement for the selected implant configuration is simulated. As noted above, the joint movement that is simulated may include an activity of daily living, which provides valuable information about how the joint will behave during ordinary use. In the context of the knee joint, the ADL may be one or more of walking, squatting, chair sitting and rising, ascending and descending stairs, and lunging. However, it is to be appreciated that joint motion other than activities of daily living may be simulated. For example, in the context of sports medicine, it may be useful to simulate a particular motion that is common to a sport in which the patient participates. In addition, all possible fragments, discrete or continuous, of the range of motion of the joint (instead of only ADLs) may be simulated.

Next, the process moves to block 512, where the predicted ligament strain for the selected ligament and/or ligament set is determined. In some embodiments, if one or more of the predicted ligament strains exceeds an upper threshold (such as 5-10% for example), the implant configuration may be rejected. Based on the predicted ligament strain, the value for the objective function may then be determined at block 514. The process then moves to decision block 516, where it is determined whether there are additional implant configurations to consider. If so, the process returns to block 508 where the next implant configuration is selected, and blocks 510, 512, and 514 are repeated, returning again to block 516. If at decision block 516 there are no additional configurations to consider, the process continues to another decision block 518. At decision block 518 it is determined whether there are additional ligaments for which the ligament behavior needs to be determined in order to determine a value for the selected objective functions. If so, the process returns to block 506 where the additional ligament or ligament set is selected. With the additional ligament or ligament set selected, the process again moves through blocks 508, 510, 512, 514, 516, and returns to decision block 518. If simulation of no additional ligaments is required at decision block 518, the process continues to block 520. There, based on the output of the simulations run, an optimal implant configuration is selected for each of the selected objective functions.

Figure 6A:
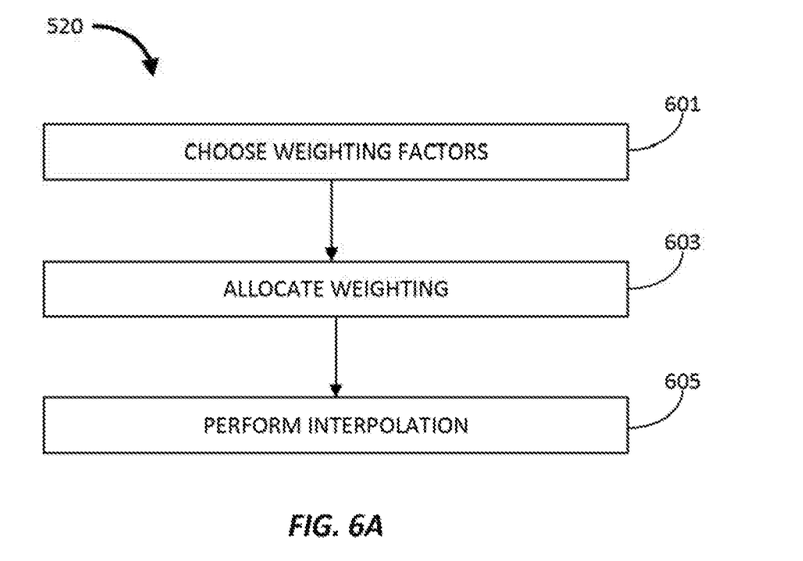
FIG. 6A is a flow chart showing illustrating a more detailed view of the selection of the best implant configuration from FIG. 5.

FIG. 6A is a flow chart illustrating a more detailed view of the selection of the best implant configuration from block 520. In particular, FIG. 6A provides an example of how an implant configuration may be determined using a combination of objective factors and interpolation. As shown, the sub process begins at block 601 where one or more weighting factors are chosen. As discussed above, the objective functions applied to the simulation data may be combined using weighting factors. Next, the process moves to block 603 where weights are allocated. For example, one objective function may be considered quite important or accurate. As a result, that particular objective function may be heavily weighted. Similarly, one of the objective functions may be considered less reliable, but still relevant. This less reliable, but still relevant objective function may be assigned a lower weight in the overall determination. Once the weights have been allocated, the process moves to block 605. There, based on the weight factors, the overall preferred implant configuration may be determined by interpolating between the selected optimal implant configurations for the different objective functions combined with the weighting factors in block 601.

Figure 6B:
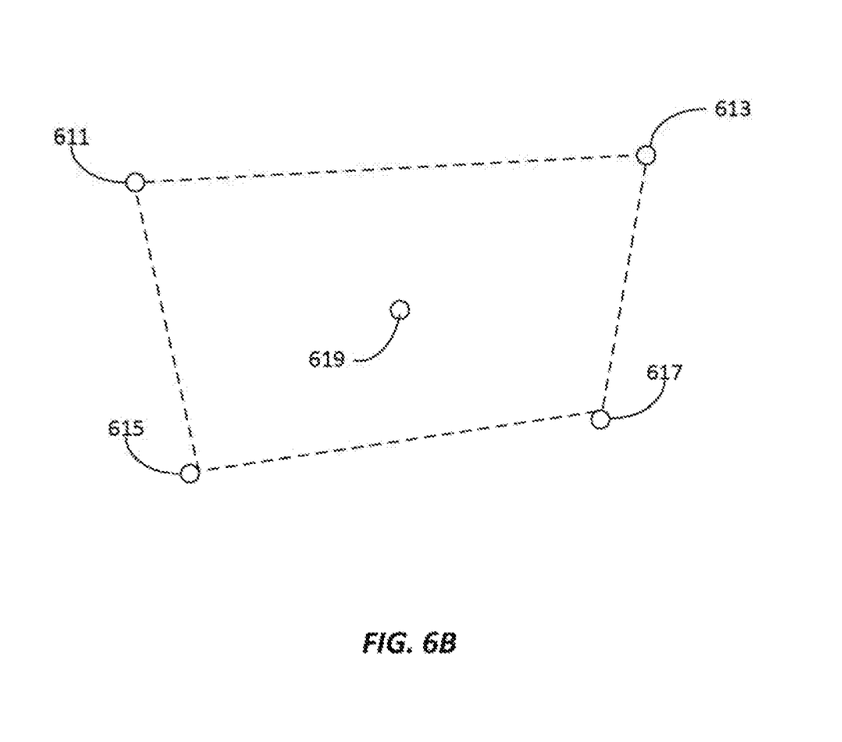
FIGS. 6B-6D provide illustrations of how the interpolating process may be carried out using differently weighted objective functions.
Figure 6C:
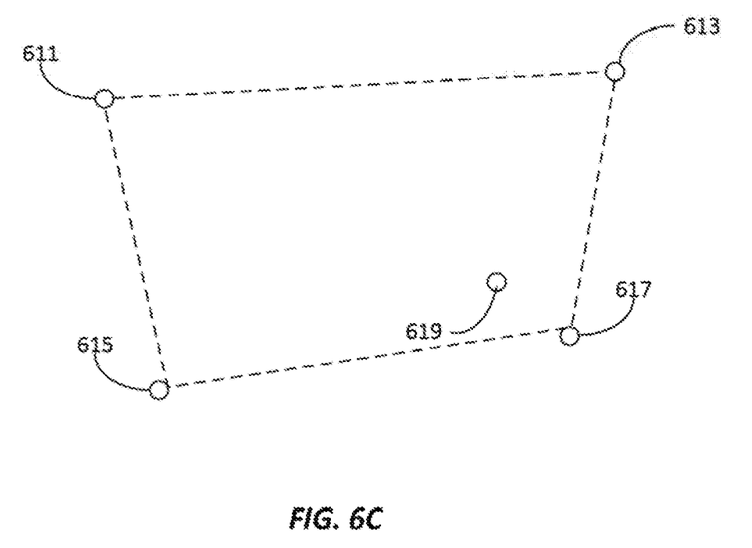
Figure 6D:
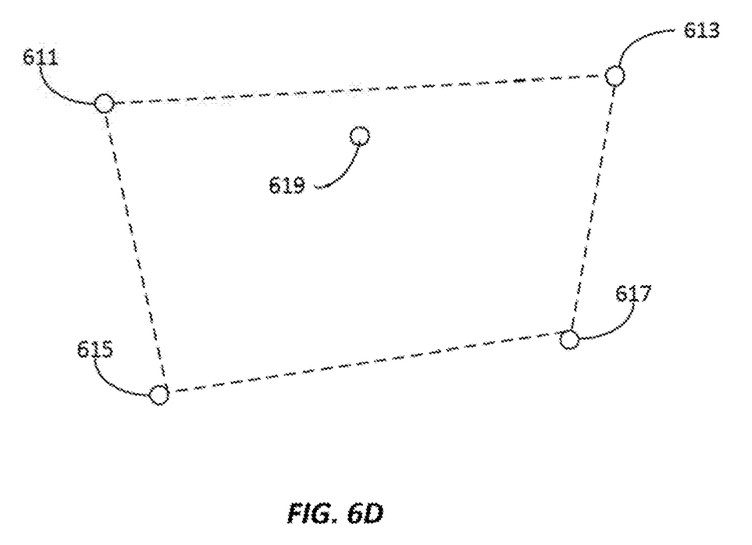

FIGS. 6B-6D provide illustrations of how the interpolating process may be carried out using differently weighted objective functions. With specific reference to FIG. 6B, a series of objective functions 611, 613, 615, and 617 are depicted as plotted values in a coordinate plane. In this particular example, each of the objective functions is given equal weight in determining the preferred implant configuration. As a result, the preferred implant configuration 619 is located in the geographical center of the four objective function points.

FIGS. 6C and 6D illustrate scenarios in which certain objective functions are given increased weight allocations. Turning to FIG. 6C, the objective functions 611, 613 and 615 each have the same value as shown above in FIG. 6B. However, in this example, objective function 617 has been allocated significantly more weight than the other objective functions. As a result of interpolating these values, the preferred implant configuration 619 is located much closer to the optimal configuration of objective function 617, which is given significantly more weight. FIG. 6D illustrates a scenario in which objective functions 611 and 613 are both heavily weighted, while objective function 615 617 are not. As a result, the preferred implant configuration 619 is located in the upper central part of the graph, generally equidistant from the optimal configurations of the heavily weighted objective functions 611 and 613, and distant from the optimal configurations of objective functions 615 and 617 which have been allocated significantly less weight in the determination.

In some embodiments, the systems and methods according to the invention comprise steps to design patient-specific surgical instruments, based on the determined implant configuration. These patient-specific surgical instruments may have one or more support features. These support features may comprise surfaces, line contacts or point contacts configured to substantially conform to a part of the anatomy of the patient, so as to provide a means of establishing a correct and stable fit of the patient-specific instrument onto the anatomy of the patient. These patient-specific surgical instruments may also have one or more functional elements. These functional elements may be attachments, indentations, bores or through-holes for the attachment or guidance of surgical instruments or implants, such as pins, screws, drills, saw blades and the like during the surgical procedure. The patient-specific surgical instruments may be used to guide or facilitate particular surgical acts, such as pin placement or the making of resections, necessary to achieve the determined implant configuration.

In some embodiments, the patient-specific surgical instruments are manufactured using an additive-manufacturing (AM) technology. AM is particularly useful for the manufacture of unique objects. AM can be defined as a group of techniques used to fabricate a tangible object typically using three-dimensional (3-D) computer-aided design (CAD) data of the object. Currently, a multitude of AM techniques is available, including selective laser sintering, stereolithography, fused deposition modeling, foil-based techniques, etc.

Selective laser sintering and selective laser melting use a high-power laser or another focused heat source to sinter or weld small particles of plastic, metal, or ceramic powders into a mass representing the 3-dimensional object to be formed. Stereolithography uses a laser to locally cure layers of resinous liquid into a solid mass. Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680. Foil-based techniques fix coats to one another by means of gluing or photo polymerization or other techniques and cut the object from these coats or polymerize the object. Such a technique is described in U.S. Pat. No. 5,192,539.

Typically, AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer-aided design and manufacturing (CAD/CAM) software.

Typically, an AM apparatus builds objects on a layer-by-layer basis. Thus, the AM apparatus proceeds in a direction perpendicular to the individual layers.

The material used to manufacture the patient-specific surgical instruments may depend on the (additive) manufacturing method used and the specifications of the instrument to be manufactured. In particular embodiments, the patient-specific surgical instruments may be made of material which is compatible with additive manufacturing, including polymeric materials, metals, metal alloys, ceramic materials and glass. In some embodiments, the patient-specific surgical instruments may be made of one or more of polyamide, polystyrene, steel, titanium, or aluminum. The patient-specific surgical instruments disclosed herein may also be made of a composite material, preferably glass-filled polyamide or alumide. Alumide is a blend of polyamide and aluminum powder. Typical materials include for instance DSM Somos® series of materials 7100, 8100, 9100, 9420, 10100, 11100, 12110, 14120 and 15100 (from DSM Somos); ABSplus-P430, ABSi, ABS-ESD7, ABS-M30, ABS-M30i, PC-ABS, PC-ISO, PC, ULTEM 9085, PPSF and PPSU materials (from Stratasys); Accura Plastic, DuraForm, CastForm, Laserform and VisiJet line materials (from 3-Systems); Aluminum, CobaltChrome and Stainless Steel materials, MarangingSteel, Nickel Alloy, Titanium, the PA line of materials, PrimeCast and PrimePart materials and Alumide and CarbonMide (from EOS GmbH).

In some embodiments, the systems and methods according to the invention comprise steps to transfer the determined implant configuration to a surgical navigation system or surgical robot. This surgical navigation system or surgical robot may be used to guide or facilitate particular surgical acts, such as pin placement or the making of resections, necessary to achieve the determined implant configuration.

Utilizing the systems and methods described above, an appropriate implant configuration may be pre-operatively determined, thereby avoiding the need for complex intraoperative ligament balancing currently prevalent in the art. Those of skill in the art will recognize at the various illustrative logical blocks, modules, and algorithm steps described in connection with the embodiments disclosed herein may be implemented as electronic hardware such as general purpose or special purpose computers, computer software running on computer hardware, or combinations thereof. To clearly illustrate this interchangeability of hardware and software, various illustrative components blocks, modules, and steps have been described above generally in terms of their functionality. Whether such functionality is implemented as hardware or software depends on the particular application and design constraints imposed on the overall system. Skilled artisans may implement the described functionality in varying ways for each particular application, but such implementation decisions should not be interpreted as causing a departure from the scope of the present invention. While the above detailed description as shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others.

What is claimed is:

1. A method of determining an implant configuration in an orthopedic arthroplasty procedure associated with a joint of a patient, the method comprising:
   (a) acquiring medical image information of the joint of the patient;
   (b) selecting an objective function;
   (c) selecting a plurality of ligaments comprising a first ligament and a second ligament associated with the joint of the patient, wherein the first ligament and the second ligament are collateral ligaments;
   (d) selecting a provisional implant configuration;
   (e) running a simulation of the joint of the patient for the selected provisional implant configuration;
   (f) determining, from the simulation, a predicted ligament strain for each of the plurality of ligaments;
   (g) determining from the predicted ligament strains a value for the objective function, wherein the objective function comprises a difference between the predicted ligament strain for the first ligament and the predicted ligament strain for the second ligament; and
   repeating the steps (d), (e), (f) and (g) for a plurality of provisional implant configurations, to determine a value for the objective function for each of the plurality of provisional implant configurations.

2. The method of claim 1, wherein the step (d) of selecting a provisional implant configuration comprises one or more of:
   selecting a position of an implant relative to the joint of the patient,
   selecting the implant from a library of implants,
   generating a design for at least part of the implant, or
   generating the design for an articulating surface of the implant.

3. The method of claim 1, further comprising:
   (h) comparing the values for the objective function for the plurality of provisional implant configurations; and
   (i) selecting, based on the values for the objective function, an implant configuration for the selected objective function.

4. The method of claim 3, further comprising repeating the steps (b), (c), (d), (e), (f), (g), (h) and (i) for a plurality of objective functions to select an implant configuration for each of the plurality of objective functions.

5. The method of claim 4, further comprising:
   (j) choosing weight factors for the plurality of objective functions; and
   (k) based on the weight factors, interpolating between the selected implant configurations for the plurality of objective functions to determine a preferred implant configuration.

6. The method of claim 1, wherein the step of acquiring medical image information of the joint of the patient comprises deriving from the medical image information a three-dimensional representation of at least part of anatomy of the patient.

7. The method of claim 6, further comprising using statistical shape models to correct the three-dimensional representation of at least part of the anatomy of the patient from a diseased condition to a healthy condition.

8. The method of claim 1, wherein the step (a) of acquiring medical image information of the joint of the patient comprises one or more of: identifying bony landmarks or reconstructing pre-operative joint alignment.

9. The method of claim 8, wherein identifying bony landmarks comprises one or more of: using statistical shape models or defining, based on the identified bony landmarks, reference systems or soft tissue attachments.

10. The method of claim 1, further comprising determining from the predicted ligament strains, a second value for a second objective function, wherein the second objective function comprises a linear combination of the predicted ligament strains.

11. The method of claim 1, further comprising determining from the predicted ligament strains, a second value for a second objective function, wherein the second objective function comprises a difference between the predicted ligament strains and native ligament strains for each of the plurality of ligaments.

12. The method of claim 11, wherein native ligament strains for the plurality of ligaments are determined without physical activity by the patient.

13. The method of claim 11, further comprising:
running a simulation of the joint of the patient without an implant; and
determining, from the simulation of the joint of the patient, native ligament strains for the plurality of ligaments.

14. The method of claim 13, wherein determining a native ligament strain comprises applying one or more of: an equation $\varepsilon=(L-Lr)/Lr$, wherein $\varepsilon$ is the native ligament strain, and wherein L is ligament length, and wherein Lr is ligament reference length; and an equation $\varepsilon=(L-L_0)/L_0$ wherein $L_0$ is ligament slack length.

15. The method of claim 14, wherein the ligament slack length $L_0$ is computed using an equation $L_0=Lr/(\varepsilon r+1)$, where Lr is the ligament reference length and $\varepsilon r$ a reference strain.

16. The method of claim 1, further comprising (h) rejecting the provisional implant configuration if at least one of the predicted ligament strains one or more of exceeds an upper threshold for the at least one predicted ligament strain or is lower than a lower threshold for the at least one predicted ligament strain.

17. The method of claim 1, wherein the step (e) of running a simulation of the joint of the patient comprises one or more of: simulating at least one discrete position for at least one degree of freedom of the joint of the patient, or simulating movement of the joint of the patient over at least part of its range of motion.

18. The method of claim 1, wherein the step (d) of selecting a provisional implant configuration comprises selecting at least one of a position or an orientation for a joint prosthesis with respect to the joint of the patient.

19. A method of determining an implant configuration in an orthopedic arthroplasty procedure associated with a joint of a patient, the method comprising:
(a) acquiring medical image information of the joint of the patient;
(b) selecting an objective function;
(c) selecting at least one ligament associated with the joint of the patient;
(d) selecting a provisional implant configuration;
(e) running a first simulation of the joint of the patient for the selected provisional implant configuration;
(f) determining from the first simulation predicted ligament strains for the at least one ligament;
(g) running a second simulation of the joint of the patient without an implant;
(h) determining from the second simulation native ligament strains for the at least one ligament;
and
(g) determining from the predicted ligament strains and native ligament strains a value for the objective function,
wherein the objective function comprises a difference between the predicted ligament strain and native ligament strain for each of the at least one ligament,
wherein determining the native ligament strains comprises applying an equation $\varepsilon=(L-L_0)/L_0$ wherein $L_0$ is ligament slack length, and
wherein the ligament slack length $L_0$ is computed using an equation $L_0=Lr/(\varepsilon r+1)$, where Lr is ligament reference length and $\varepsilon r$ a reference strain.

* * * * *